(12) United States Patent
Iddan et al.

(10) Patent No.: US 6,764,440 B2
(45) Date of Patent: *Jul. 20, 2004

(54) ENERGY MANAGEMENT OF A VIDEO CAPSULE

(75) Inventors: Gavriel J. Iddan, Haifa (IL); Gavriel Meron, Petach Tikva (IL)

(73) Assignee: Given Imaging Ltd., Yoqneam (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/946,937

(22) Filed: Sep. 6, 2001

(65) Prior Publication Data

US 2002/0032366 A1 Mar. 14, 2002

Related U.S. Application Data

(63) Continuation of application No. 09/581,628, filed as application No. PCT/IL98/00608 on Dec. 15, 1998, now Pat. No. 6,428,469.

(30) Foreign Application Priority Data

Dec. 15, 1997 (IL) .................................................. 122602

(51) Int. Cl.[7] .............................................. A61B 1/045
(52) U.S. Cl. ....................... 600/109; 600/118; 600/117; 348/76
(58) Field of Search ................................ 600/109, 117, 600/118, 160, 407, 476; 348/65, 76, 82, 84; 955/86, 95, 100; 306/17

(56) References Cited

U.S. PATENT DOCUMENTS

| | | | |
|---|---|---|---|
| 4,149,769 | A | 4/1979 | Zobel |
| 4,278,077 | A | 7/1981 | Mizumoto |
| 5,267,033 | A | 11/1993 | Hoshino |
| 5,279,607 | A | 1/1994 | Schentag et al. |
| 5,441,041 | A | 8/1995 | Sauer et al. |

(List continued on next page.)

FOREIGN PATENT DOCUMENTS

| | | | | |
|---|---|---|---|---|
| DE | 29 41 363 | | 4/1981 | |
| DE | 34 40 177 | | 5/1986 | |
| DE | 197 23 454 A1 | * | 12/1998 | ........... G08B/13/02 |
| EP | 0 667 115 | | 5/1995 | |
| WO | WO 99/30610 | * | 6/1999 | ............ A61B/5/00 |

OTHER PUBLICATIONS

Wireless transmission of a color television moving image from the stomach using a miniature CCD camera, light source and microwave transmitter, Swain CP, Gong F, Mills TN. Gastrointest Endosc 1997;45:AB40.

(List continued on next page.)

*Primary Examiner*—John P. Leubecker
(74) *Attorney, Agent, or Firm*—Eitan, Pearl, Latzer & Cohen Zedek, LLP

(57) ABSTRACT

An energy saving device for acquiring in vivo images of the gastro-intestinal tract is provided. The device, such as an autonomous capsule, includes at least one imaging unit; a control unit connected to the imaging unit and a power supply connected to the control unit. The control unit includes a switching unit and an axial motion detector connected to the switching unit. The axial motion detector detects the axial movement of the device and if the axial acceleration is below a pre-determined threshold, disconnects the power supply thereby preventing the acquisition of redundant images.

10 Claims, 4 Drawing Sheets

U.S. PATENT DOCUMENTS

| | | | |
|---|---|---|---|
| 5,551,947 A | | 9/1996 | Kaali |
| 5,569,292 A | | 10/1996 | Scwemberger et al. |
| 5,572,252 A | * | 11/1996 | Naka et al. ............ 348/208.16 |
| 5,596,366 A | * | 1/1997 | Takashima et al. .... 348/208.16 |
| 5,604,531 A | | 2/1997 | Iddan et al. |
| 5,681,260 A | | 10/1997 | Ueda et al. |
| 5,819,736 A | | 10/1998 | Avny et al. |

OTHER PUBLICATIONS

Manual of Photogrammetry, Thompson (Ed.), Third Edition, vol. Two, American Society of Photogrammetry, 1966 (Third Edition).

"Heidelberger Kapsel" —ein Kleinstsender für die pH–Messung im Magen, Lange, et al., Telefunken–Zeitung, Jg 36 (1963) Heft 5, pp. 265–270.

The Radio Pill, Rowlands, et al., British Communications and Electronics, Aug. 1960, pp. 598–601.

Evaluation of the Heidelberg pH Capsule, Yarbrough, et al., The American Journal of Surgery, vol. 117, Feb. 1969, pp. 185–192.

Bio–Medical Telemetry, R. Stuart Mackay, John Wiley & Sons, Inc. 1968.

* cited by examiner

ENERGY MANAGEMENT OF A VIDEO CAPSULE

The present application is a continuation of prior U.S. application Ser. No. 09/581,628 filed on Aug. 16, 2000 and entitled "Energy Management of a Video Capsule", now U.S. Pat. No. 6,428,469, which in turn claims priorty from prior International Application PCT/IL98/00608 filed on Dec. 15, 1998.

FIELD OF THE INVENTION

The present invention concerns a management system for controlling the energy expenditure of autonomous video capsules. More specifically, the invention is in the field of internal medical inspection of the gastro-intestinal tract.

BACKGROUND OF THE INVENTION

Endoscopic inspection is a common practice in the medical diagnosis of gastrointestinal (G.I.) diseases. The video camera used for identifying observable irregularities of the internal lining of the G.I. tract is installed within an endoscope and progressive scenes are observed by pushing the endoscope inside the tract. The endoscope is a tubular device typically containing either a camera with the associated electric circuits or a fiber-optic image guide. It also includes a light source or a light guide, and an electrical conductor for accepting signals and\or supplying energy. Because the movement of the endoscope head along the G.I. tract is brought about by a pushing action, the mechanical impact associated with such application of force become especially adverse as soon as the head of the endoscope enters a bend. In such bends, the movement of the endoscope is greatly impeded, risking the G.I. tract walls, which are susceptible to perforation, and limiting the method of endoscopic inspection to non-convoluted regions of the G.I. tract.

An in-vivo autonomous video capsule, described in U.S. Pat. No. 5,604,531 whose disclosure is incorporated herein by reference, moves along the G.I. tract by virtue of the natural squeezing action of the tract's walls, thus overcoming the risk of the pushing action, and, in addition, offering a more convenient method of administering the camera. An additional benefit of the capsule is avoiding the cumbersome aspects of connecting the intestines of the patient to external appliances. Via the autonomous capsule, images of the gastro-intestinal tract are obtained without physical connections being made to an energy source or an information drain. An internal power supply energizes the capsule and supports the illumination, image acquisition and radio transmission of the information to an external receiver. Because of the considerable length of the G.I. tract, many images have to be acquired in order to cover the entire length of the tract, this amount of data may be augmented by redundant images of the same site which are acquired when the capsule stops moving or is only barely doing so. Such a task consumes a substantial amount of energy, thus potentially becoming a limiting factor in respect of quality and quantity of the set of images collected in a single inspection. An additional drawback connected with redundancy of images of a G.I. tract is the effectivity of analysis stage. Once the entire sequence of images is presented to the analyzing physician, a lengthy process of finding the potential sites of interest ensues. Any redundancy existing in such a sequence of images poses a disturbance to analysis procedure.

SUMMARY OF THE PRESENT INVENTION

It is an object of the present invention to provide a device to be incorporated in an autonomous capsule, used for the inspection of the G.I. tract, which minimizes energy expenditure of the imaging unit of the capsule.

In accordance with a preferred embodiment of the invention, the capsule which obtains in vivo images of the G.I. tract internally, includes at least one imaging unit; a control unit connected to the imaging unit and a power supply connected to the control unit. The control unit includes a switching unit and an axial motion detector connected to the switching unit. The axial motion detector detects the axial movement of the device and if the axial acceleration is below a pre-determined threshold, disconnects the power supply thereby preventing the acquisition of redundant images.

Furthermore, in accordance with a preferred embodiment of the invention, the axial motion detector includes an accelerometer, an amplifier connected to the accelerometer for amplifying the signal from the accelerometer and an analyzer connected to the amplifier, for analyzing the amplified signal. The analyzer includes a comparator for comparing the analyzed signal with a pre-determined threshold.

In addition, in accordance with a preferred embodiment of the invention, a method for reducing redundant image acquisition of the internal gastro-intestinal tract by an imaging unit residing within a capsule within the tract is provided. The method includes the steps of:

detecting the axial motion of the capsule; and if the detected motion is below a pre-determined threshold disconnecting the imaging unit.

Furthermore, in accordance with a preferred embodiment of the invention, the method further include a the step of reconnecting the imaging unit if the detected motion is above the pre-determined threshold.

BRIEF DESCRIPTION OF THE DRAWINGS

The present invention will be understood and appreciated more fully from the following detailed description taken in conjunction with the appended drawings in which.

DETAILED DESCRIPTION OF THE INVENTION

Figure 1:
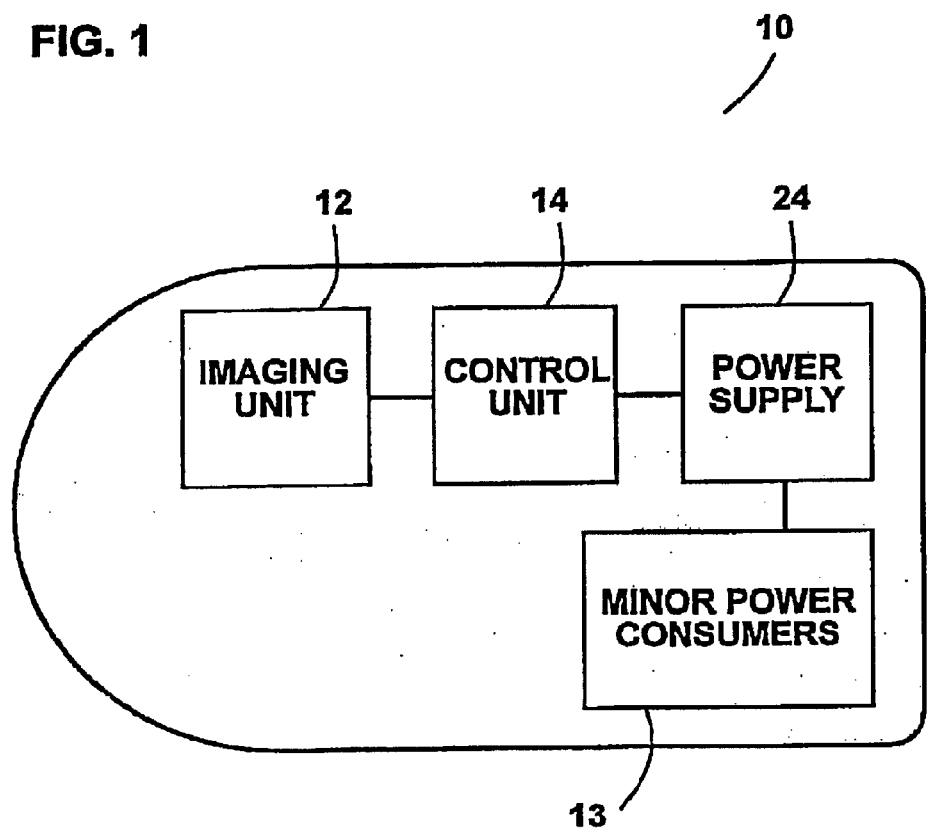
FIG. 1 is a schematic block diagram illustration of the structure of a motile video camera residing inside an autonomous capsule.

Reference is now made to FIG. 1. which shows the schematic structure of an autonomous capsule 10 containing a control unit 14 for controlling energy flow from a power supply 24 to the major power consumer in the capsule which is an imaging unit 12. Minor power consumers 13 are not subjected to the intervention of unit 14. The power supply 24 of the autonomous capsule, is therefore connected to the imaging unit 12 indirectly, thus subjecting the flow of energy to the control exerted by the control unit 14. The autonomous capsule, containing its own limited supply of energy, travels the entire length of the G.I. tract acquiring a potentially large amount of images on the entire length of the tract. Therefore the present invention minimizes the amount of energy consumed consistent with the acquisition of as much valuable information as possible.

Figure 2:
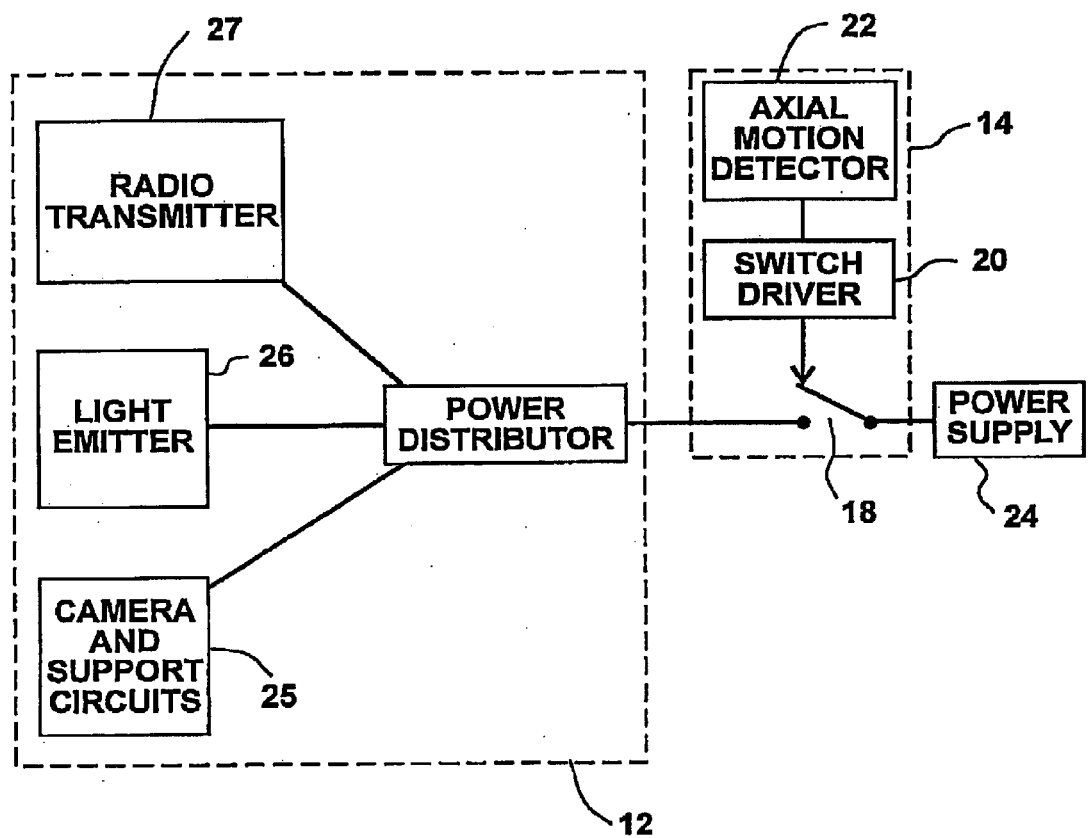
FIG. 2 is a schematic block diagram illustration showing with details the imaging and the control unit which regulates its power consumption.

FIG. 2. to which reference is now made, shows among other units, the details of the control unit 14 and imaging unit 12. Other embodiments, providing the same energy economizing effect, are included in the present invention.

Unit 14 comprises an axial motion detector 22, a switch driver 20, and an on/of switch 18. The axial motion detector 22 detects the movement changes of the capsule and extracts the axial movement component of the capsule. If the conditions of a prescribed decision rule have been met, an actuation command is sent to switch driver 20. That is, the switching unit 18 either connects or disconnects the power supply 24. The imaging unit comprises three major power consumers, namely radio transmitter 27, illuminator (light emitter) 26, and camera assembly 25. Power distributor 16 controls the supply to these consumers.

Figure 3:
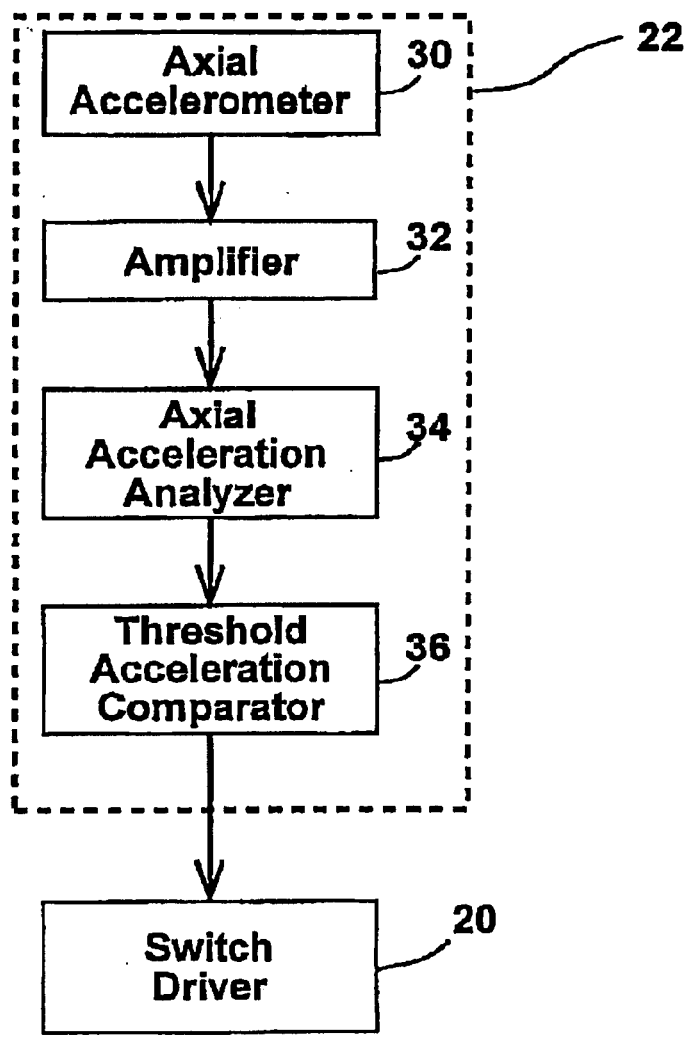
FIG. 3 is a block diagram illustration showing in detail the components of the motion detector which initiates the sequence of events leading the changes in the switching status of the energy supply.

FIG. 3, to which reference is now being made, is a detailed schematic illustration of the axial motion detector 22. The detector 22 comprises an axial accelerometer 30, which is connected to an amplifier 32 for amplifying the signal. The enhanced signal is processed by an axial acceleration analyzer 34. The value provided by this analyzer is sent to a threshold acceleration comparator 36 which passes information to the switch driver 20.

The linear accelerometer 30 is selectively sensitive to accelerations in the axial direction of the body of the accelerometer. It therefore has to be physically aligned with the motion axis of the capsule.

The procedure may be described as follows; The output signal from the accelerometer 30 is first amplified by unit 32, and then provided to analyzer 34 which determines the actual axial acceleration. Comparator 36 compares the acceleration value to a predetermined threshold value and decides whether to change the switch. Thus, upon deceleration of the capsule relative to the G.I. tract, the axial accelerometer would indicate a negative acceleration. The magnitude of the signal is analyzed by unit 34 and a threshold comparison is performed by comparator 36. If the input is above the threshold value, the power supply is disconnected via a command from driver 20.

Similarly, if a dormant capsule suddenly starts moving, the signal provided by the accelerometer 30 is analyzed and compared to the threshold figure. If the value indicates, the power supply is reconnected to re-activate the imaging unit 12.

Figure 4:
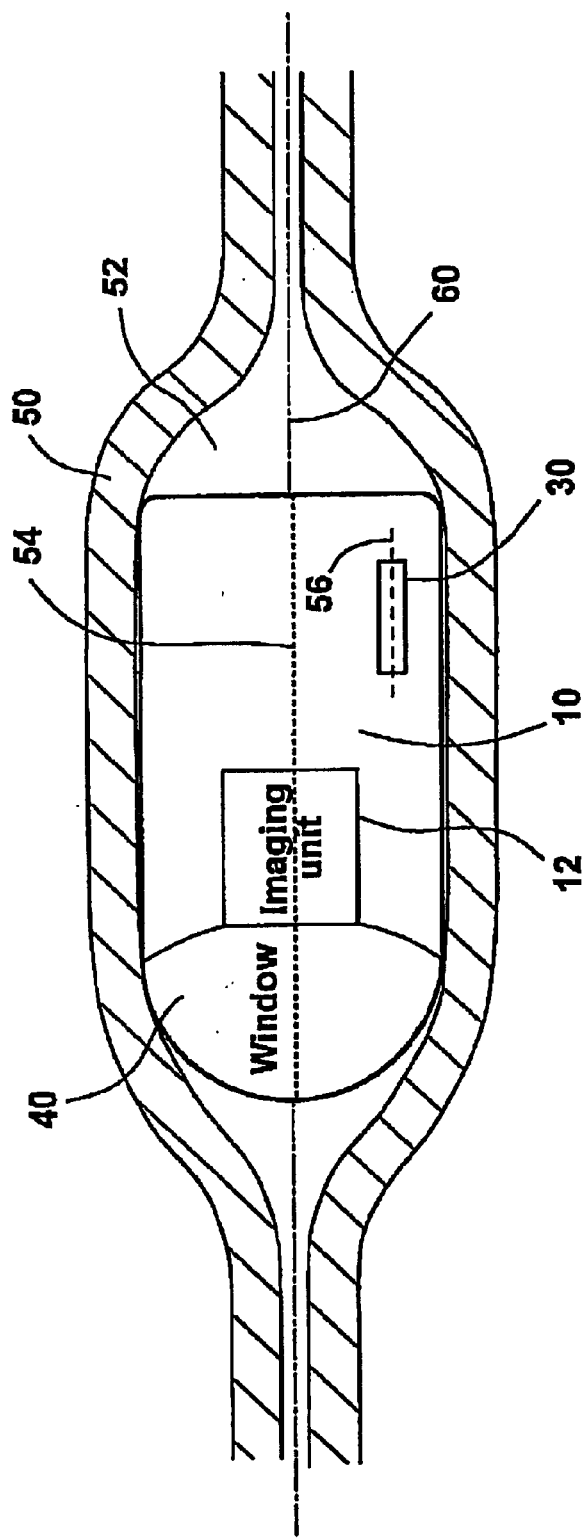
FIG. 4 is an illustration showing the positioning of the autonomous capsule within the G.I. tract.

The alignment of the motion axis of the capsule is illustrated in FIG. 4, which shows some of the structures of the capsule 10. The capsule 10 moves along the contracted void 52 of the G.I. tract 56 by the squeezing action of the walls 50 of the G.I. tract. This causes the longitudinal axis (referenced 54) of the capsule to align along the local axis 60 of the G.I. tract. In order for the axial accelerometer 30 to detect the progressive motion within the G.I. tract, its longitudinal axis, referenced 56, must be aligned in parallel with the longitudinally overlapping axes (54, 60) of the capsule and the G.I. tract, respectively.

False alarms arising from body movements having a component in the axial direction of the capsule could also actuate an otherwise dormant capsule, if the signal amplitude is above a predefined threshold occurs. In an alternative embodiment, in order to detect such body movements an external detector can be employed in addition to the internal accelerometer of the capsule.

It will be appreciated by persons skilled in the art that the present invention is not limited by what has been particularly shown and described herein above. Rather the scope of the invention is defined by the claims which follow:

What is claimed is:

1. An in vivo device for acquiring in vivo images, said device comprising:

at least one imaging unit;

a control unit connected to said at least one imaging unit, said control unit comprising:

a switching unit; and a motion detector connected to said switching unit;

wherein said control unit is to, in response to a signal from the motion detector, disconnect a power supply from the device.

2. A device according to claim 1 wherein said motion detector comprises:

an accelerometer.

3. The device of claim 2, comprising an axial accelerometer.

4. The device of claim 1, comprising:

an amplifier; and an analyzer connected to said amplifier.

5. A device according to claim 4 wherein said analyzer comprises a comparator to compare an analyzed signal with a pre-determined threshold.

6. The device of claim 1, wherein the device is a swallowable capsule.

7. The device of claim 1, comprising a transmitter.

8. The device of claim 1, wherein the device is capable of imaging the gastrointestinal tract.

9. A system comprising:

the device of claim 1; and a second motion detector disposed external to a body being examined.

10. The device of claim 1, comprising a power supply.

* * * * *